US008954291B2

(12) United States Patent
Messenger et al.

(10) Patent No.: US 8,954,291 B2
(45) Date of Patent: Feb. 10, 2015

(54) ALARM SETTING AND INTERFACING WITH GESTURE CONTACT INTERFACING CONTROLS

(71) Applicant: Fitbit, Inc., San Francisco, CA (US)

(72) Inventors: Jayson Messenger, San Francisco, CA (US); Shelten Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/329,735

(22) Filed: Jul. 11, 2014

(65) Prior Publication Data

US 2014/0320284 A1 Oct. 30, 2014

Related U.S. Application Data

(60) Continuation-in-part of application No. 13/959,714, filed on Aug. 5, 2013, now Pat. No. 8,762,101, which is a continuation-in-part of application No. 13/693,334, filed on Dec. 4, 2012, now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, said application No. 13/959,714 is a continuation-in-part of application No. 13/759,485, filed on Feb. 5, 2013, now Pat. No. 8,543,351, which is a division of application No. 13/667,229, which is a division of application No. 13/469,027, which is a division of application No. 13/246,843, which is a division of application No. 13/156,304, application No. 14/329,735, which is a continuation of application No. 14/050,305, filed on Oct. 9, 2013, now Pat. No. 8,812,259.

(60) Provisional application No. 61/388,595, filed on Sep. 30, 2010, provisional application No. 61/390,811, filed on Oct. 7, 2010, provisional application No. 61/886,000, filed on Oct. 2, 2013.

(51) Int. Cl.
*G06F 19/00* (2011.01)
*G08B 25/00* (2006.01)

(52) U.S. Cl.
CPC .................................. *G08B 25/008* (2013.01)
USPC ....................................................... 702/160

(58) Field of Classification Search
CPC ............................... G01G 19/44; G06F 19/32
USPC .................. 702/160, 150, 155, 182–185, 188
See application file for complete search history.

(56) References Cited

U.S. PATENT DOCUMENTS

2007/0179761 A1* 8/2007 Wren et al. ....................... 703/2

*Primary Examiner* — Edward Raymond
(74) *Attorney, Agent, or Firm* — Martine Penilla Group, LLP

(57) ABSTRACT

A device configured for capture of activity data for a user includes a housing, a sensor, a motor, a memory, and a processor. The sensor is disposed in the housing to capture physical contact upon the housing. The motor causes vibration of the housing. The memory stores an alarm setting that defines a time of day for triggering an alarm on the device. The processor activates the alarm upon reaching the time of day defined by the alarm setting, with the alarm causing the motor to produce the vibration of the housing. The sensor, which is interfaced with the processor, is configured to detect a physical contact upon the housing. The processor is configured to deactivate the alarm if the physical contact qualifies as an input to deactivate the alarm. The deactivating of the alarm causes the vibration of the device to be suspended.

30 Claims, 10 Drawing Sheets

ALARM SETTING AND INTERFACING WITH GESTURE CONTACT INTERFACING CONTROLS

CLAIMS OF PRIORITY

This application is a continuation of U.S. patent application Ser. No. 14/050,305, entitled "Alarm Setting and Interfacing with Gesture Contact Interfacing Controls," filed on Oct. 9, 2013, which claims priority to U.S. Provisional Application No. 61/886,000, entitled "Alarm Setting and Interfacing with Gesture Contact Interfacing Controls," filed on Oct. 2, 2013, and which is incorporated herein by reference.

This application is a continuation-in-part of U.S. patent application Ser. No. 13/959,714, filed on Aug. 5, 2013, titled "Methods and Systems for Identification of Event Data Having Combined Activity and Location Information of Portable Monitoring Devices," which is a continuation-in-part of U.S. patent application Ser. No. 13/693,334 (now issued as U.S. Pat. No. 8,548,770, issued on Oct. 1, 2013), filed on Dec. 4, 2012, titled "Portable Monitoring Devices and Methods for Operating Same," which is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same," which is a divisional of U.S. patent application Ser. No. 13/469,027, now U.S. Pat. No. 8,311,769, filed on May 10, 2012, titled "Portable Monitoring Devices and Methods for Operating Same," which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same," which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same," and to U.S. Provisional Patent Application No. 61/390,811, filed on Oct. 7, 2010, and titled "Portable Monitoring Devices and Methods for Operating Same," all of which are hereby incorporated by reference in their entirety.

This application is a continuation-in-part of U.S. patent application Ser. No. 13/959,714, filed Aug. 5, 2013, titled "Methods and Systems for Identification of Event Data Having Combined Activity and Location Information of Portable Monitoring Devices," which is a continuation-in-part of U.S. patent application Ser. No. 13/759,485, (now issued as U.S. Pat. No. 8,543,351, issued on Sep. 24, 2013), filed on Feb. 5, 2013, titled "Portable Monitoring Devices and Methods for Operating Same," which is a divisional of U.S. patent application Ser. No. 13/667,229, filed on Nov. 2, 2012, titled "Portable Monitoring Devices and Methods for Operating Same," which is a divisional of U.S. patent application Ser. No. 13/469,027, now U.S. Pat. No. 8,311,769, filed on May 10, 2012, titled "Portable Monitoring Devices and Methods for Operating Same," which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same," which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same," all of which are hereby incorporated by reference in their entirety.

CROSS REFERENCE TO RELATED APPLICATION

This application is related to U.S. application Ser. No. 14/050,292, now U.S. Pat. No. 8,744,803, filed on Oct. 9, 2013, entitled "Methods, Systems, and Devices for Activity Tracking Device Data Synchronization with Computing Devices," which claims priority to U.S. Provisional Application No. 61/885,962, filed on Oct. 2, 2013, both of which are incorporated herein by reference.

FIELD

The present disclosure relates to systems and methods for capturing activity data over a period of time and methods and systems for configuring alarm settings in activity tracking devices.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces.

It is in this context that embodiments described herein arise.

SUMMARY

Embodiments described in the present disclosure provide systems, apparatus, computer readable media, and methods for configuring alarm setting for activity tracking devices using remote computing devices and transferring the configured alarm settings to the activity tracking devices. Some embodiments are directed toward the use of contact gestures either to transition an alarm of the activity tracking device into a snooze mode or to turn the alarm off.

In one embodiment, a method, which is executed by a processor, is provided. The method includes receiving an alarm setting that defines a time of day for triggering an alarm on a device for tracking activity data of a user, and activating the alarm upon reaching the time of day defined by the alarm setting. The alarm produces a vibration of the activity tracking device. The method further includes using a sensor to detect a physical contact upon the device, and deactivating the alarm if the physical contact qualifies as an input to deactivate the alarm. The deactivating of the alarm causes the vibration of the activity tracking device to be suspended.

In one embodiment, the suspension of the vibration of the activity tracking device transitions the alarm into either a snooze mode or an off mode. In one embodiment, the snooze mode continues for a predetermined period of time before reactivating the alarm. In one embodiment, the method further includes transitioning into the snooze mode one or more times until entering the off mode or processing the vibration for a threshold period of time.

In one embodiment, the physical contact is a result of one or more taps on a surface of the activity tracking device. In one embodiment, a snooze mode, which causes the vibration to be suspended, is entered when the physical contact is represented by a single tap onto a surface of the activity tracking device, or a double tap onto the surface of the device, or three taps onto the surface of the device, or four taps onto the surface of the device, or a predetermined set of repeated taps onto the surface of the device. In one embodiment, two or more of the taps are received within a predetermined period of time to qualify as an input.

In one embodiment, the method further includes transitioning from the snooze mode to an off mode when an additional physical contact is sensed by the sensor. The additional physical contact can be represented by a single tap onto a surface of the activity tracking device, or a double tap onto the surface of the device, or three taps onto the surface of the device, or four taps onto the surface of the device, or a predetermined set of repeated taps onto the surface of the device. In one embodiment, two or more of the taps are received within a predetermined period of time to qualify as an input.

In one embodiment, the method further includes transitioning from the snooze mode to an off mode when the processor of the activity tracking device determines that a button of the device is pressed.

In one embodiment, the alarm setting is received wirelessly from a computing device. In one embodiment, the computing device has access to the Internet. In one embodiment, the alarm setting is programmable at a website managed by a server, and the website is managed by the server to allow access to user accounts, with each user account having associated therewith one or more of the activity tracking devices, such that the alarm setting is custom set in a user account In one embodiment, the alarm setting is transferred from the server to the computing device over the Internet and from the computing device to the device via a wireless Bluetooth connection. In one embodiment, the activity data of the user includes metrics associated with one or more of step count metrics, or stair count metrics, or distance traveled metrics, or active time metrics, or calories burned metrics, or sleep metrics.

In another embodiment, a device configured for capture of activity data for a user is provided. The device includes a housing, a sensor, a motor, a memory, and a processor. The sensor is disposed in the housing to capture physical contact upon the housing. The motor causes vibration of the housing of the device. The memory stores an alarm setting that defines a time of day for triggering an alarm on the device. The processor activates the alarm upon reaching the time of day defined by the alarm setting, with the alarm causing the motor to produce the vibration of the housing. The sensor, which is interfaced with the processor, is configured to detect a physical contact upon the housing of the device. The processor is configured to deactivate the alarm if the physical contact qualifies as an input to deactivate the alarm. The deactivating of the alarm causes the vibration of the device to be suspended.

In one embodiment, the housing is part of a wearable wrist attachable structure, or an attachable structure that can be carried or worn by the user. In one embodiment, the wearable wrist attachable structure is defined at least partially from a plastic material. In one embodiment, the physical contact captured by the sensor is from one or more taps upon the housing by a finger or hand. In one embodiment, the housing includes a button, and the physical contact upon the housing of the device is not from a button press.

In one embodiment, the housing further includes wireless communication logic. In one embodiment, the wireless communication logic includes one of WiFi processing logic, or Bluetooth (BT) processing logic, or radio processing logic. In one embodiment, the wireless communication logic is configured to pair with a portable computing device or a computer, and the portable computing device or the computer is configured for communication over the Internet with a server, the server having processing instructions for configuring the alarm settings.

In one embodiment, the processor examines predefined motion profiles captured by the sensor to qualify the physical contact as the input, such that motion profiles outside of the predetermined motion profiles do not qualify as the input. In one embodiment, suspending the vibration of the device transitions the alarm into one of a snooze mode or an off mode. In one embodiment, the processor configures the snooze mode to continue for a predetermined period of time before reactivating the alarm, and the processor transitions into the snooze mode one or more times until entering the off mode or processing the vibration for a threshold period of time.

In one embodiment, the physical contact is the result of one or more taps on a surface of the device. In one embodiment, two or more of the taps are received within a predetermined period of time to qualify as the input. In one embodiment, the processor causes a snooze mode, which causes the vibration to be suspended, to be entered when the physical contact is represented by a single tap onto a surface of the device, or a double tap onto the surface of the device, or three taps onto the surface of the device, or four taps onto the surface of the device, or a predetermined set of repeated taps onto the surface of the device.

In yet another embodiment, one or more non-transitory computer readable media are provided. The one or more computer readable media include instructions which, when executed by a processor, perform the following operations: receiving an alarm setting that defines a time of day for triggering an alarm on a device for tracking activity data of a user; activating the alarm upon reaching the time of day defined by the alarm setting, the alarm producing a vibration of the device; using a sensor to detect a physical contact upon the device; and deactivating the alarm if the physical contact qualifies as an input to deactivate the alarm, the deactivating causing the vibration of the device to be suspended.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings in which.

DETAILED DESCRIPTION

Embodiments described in the present disclosure provide systems, apparatus, computer readable media, and methods for configuring alarm setting for activity tracking devices using remote computing devices and transferring the configured alarm settings to the activity tracking devices. Some embodiments are directed toward the use of contact gestures either to transition an alarm of the activity tracking device into a snooze mode or to turn the alarm off.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

Figure 1A:
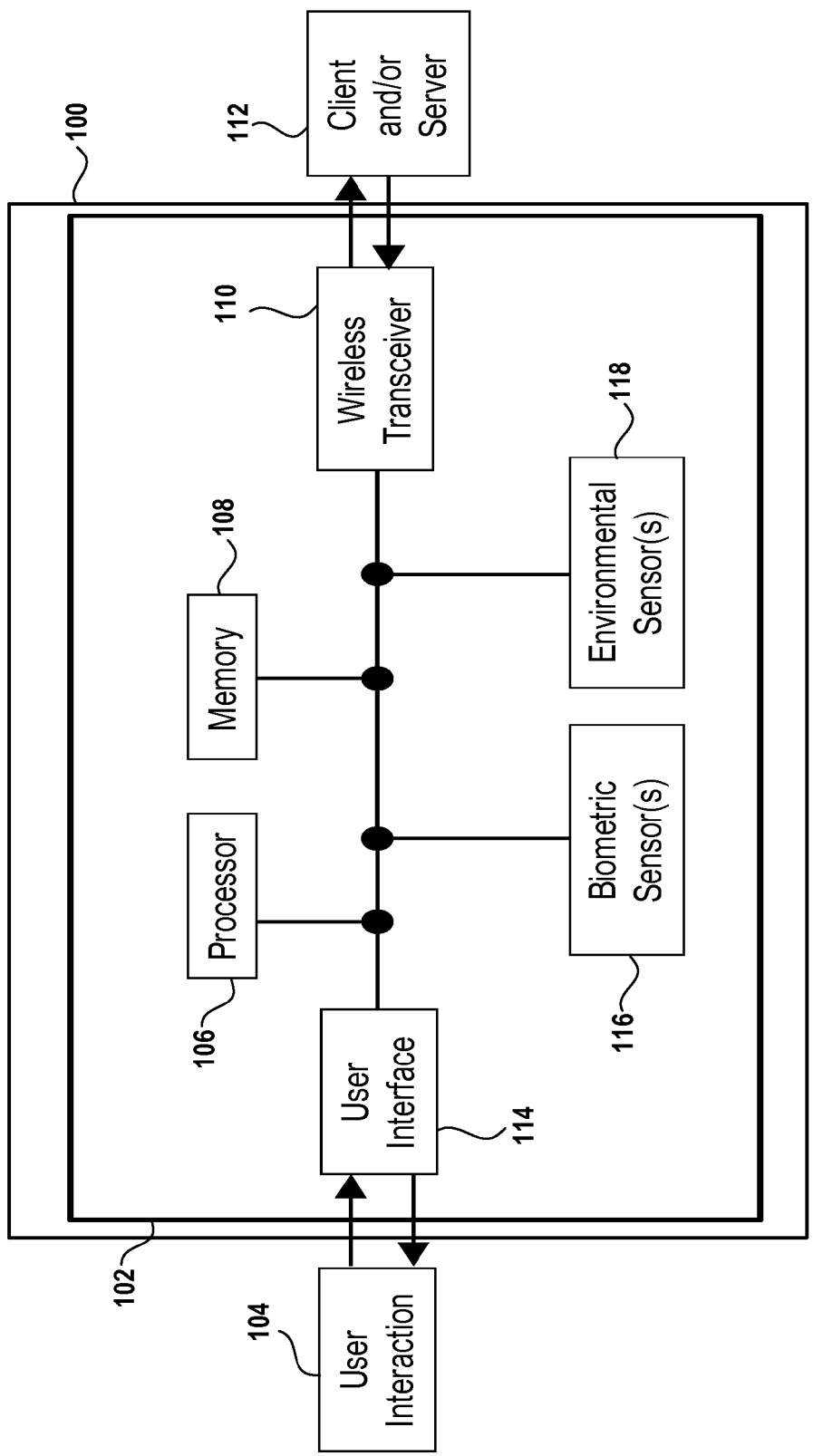
FIG. 1A shows a block diagram of an activity tracking device, in accordance with one embodiment of the present invention.

FIG. 1A shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 that is in the form of noncontact input. The noncontact input can be by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. As will be explained in more detail below, the physical contact may be in the form of a tap or multiple taps by a finger upon the housing of the activity tracking device 100.

Figure 1B:
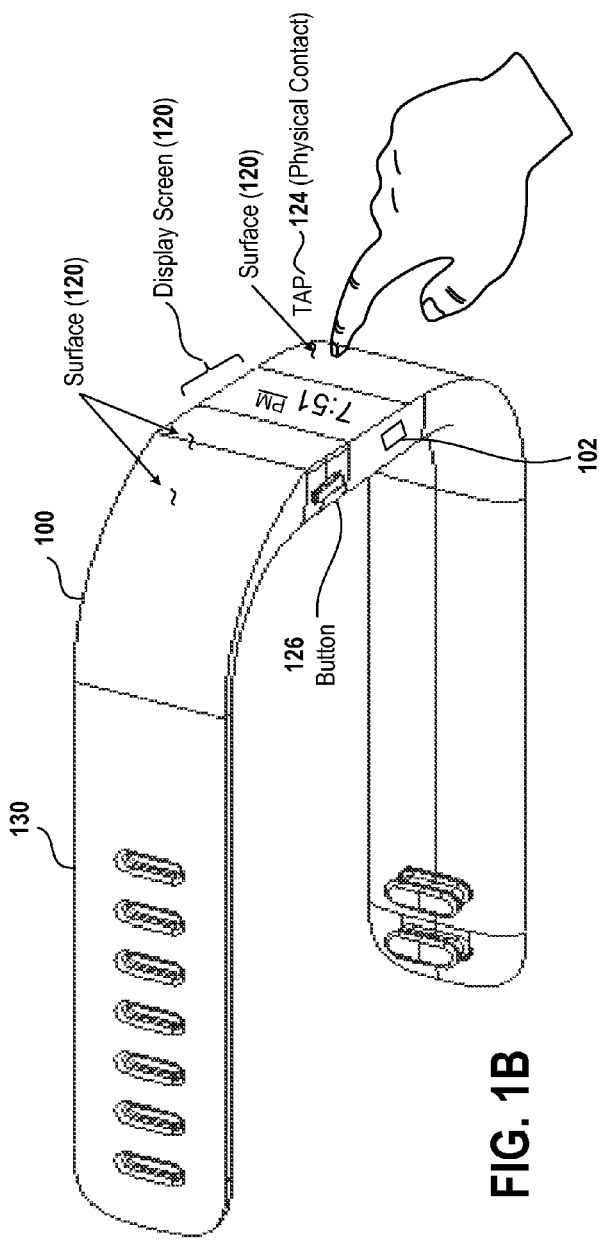
FIG. 1B illustrates an example of an activity tracking device, in accordance with one embodiment of the present invention.

FIG. 1B illustrates an example of an activity tracking device 100 having a housing 130 in the form of a wearable wrist attachable device. The sensors of the activity tracking device 100 can, as mentioned above, detect motion such as physical contact that is applied and received on a surface 120 of the housing 130. In the example shown, the physical contact 124 is in the form of a tap or multiple taps on the surface 120. Device components 102 are, in one embodiment, contained within the housing 130. The location at which the device components 102 are integrated into the housing 130 can vary. For example, the device components 102 can be integrated throughout various locations around the housing 130, and not limited to the central portion of the wrist attachable device. In some embodiments, the device components 102 can be integrated into or with a smart watch device.

In other embodiments, the device components 102 are positioned substantially in a central position of the wrist attachable device, such as under or proximate to a location where a display screen 122 is located. In the illustrated example, the housing 130 also includes a button 126. The button 126 can be pressed to activate the display screen 122, navigate to various metrics displayed on the screen 122, or turn off the screen 122.

Figure 1C:
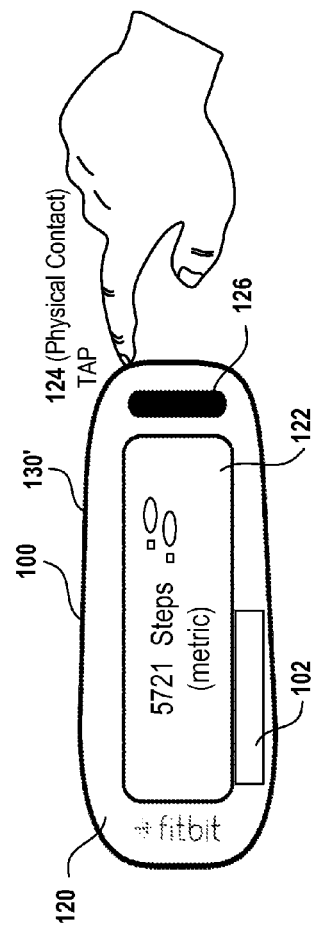
FIG. 1C illustrates another example of an activity tracking device, in accordance with one embodiment of the present invention.

FIG. 1C illustrates another example of an activity tracking device 100, in accordance with one embodiment of the present invention. The form factor of the activity tracking device 100 is shown as a clickable device that includes a screen 122, a button 126, and device components 102 integrated within the housing 130'. The housing 130' can include a clip that allows for attachment to clothing or articles of the user, or to simply place the device within a pocket or holder of the user. Accordingly, the physical contact 124 shown with respect to FIG. 1B can also be implemented upon the surface 120 of activity tracking device 100 of FIG. 1C. It should be understood, therefore, that the form factor of the activity tracking device 100 can take on various configurations and should not be limited to the example configurations provided herein.

Figure 2A:
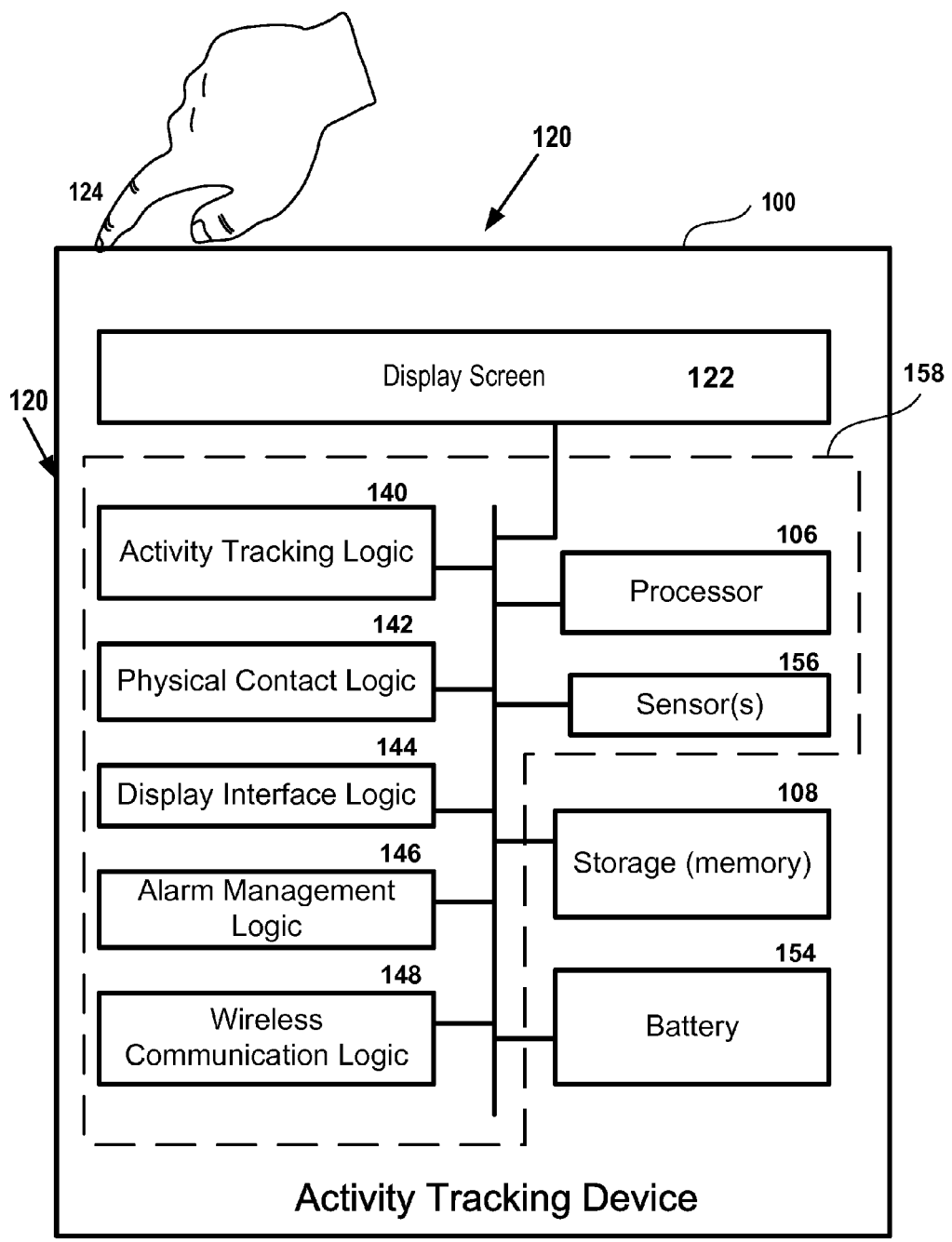
FIG. 2A illustrates an example of activity tracking device including example components utilized for tracking activity and motion of the device, and associated interfaces to a display screen, in accordance with one embodiment of the present invention.

FIG. 2A illustrates an example of activity tracking device 100 of FIG. 1A, showing some additional example components utilized for tracking activity and motion of the device, and associated interfaces to display screen 122. In this example, the finger of a user can be used to tap and provide physical contact 124 onto any surface 120 of activity tracking device 100. The physical contact, when sensed by sensors 156 of the activity tracking device 100, will cause a response by the activity tracking device 100, and therefore provide some metric on the display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 2A, the activity tracking device 100 includes logic 158. Logic 158 may include activity tracking logic 140, physical contact logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

In other embodiments, the physical contact logic can be programmed to determine when particular physical contacts occurred, the time in between the physical contacts, and whether the one or more physical contacts will qualify within predefined motion profiles that would indicate that an input is desired. If physical contact occurs that is not within some predefined profile or pattern, the physical contact logic will not indicate or qualify that physical contact as an input.

The display interface logic 144 is configured to interface with the processor and the physical contact logic to determine when specific metric data will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 2B:
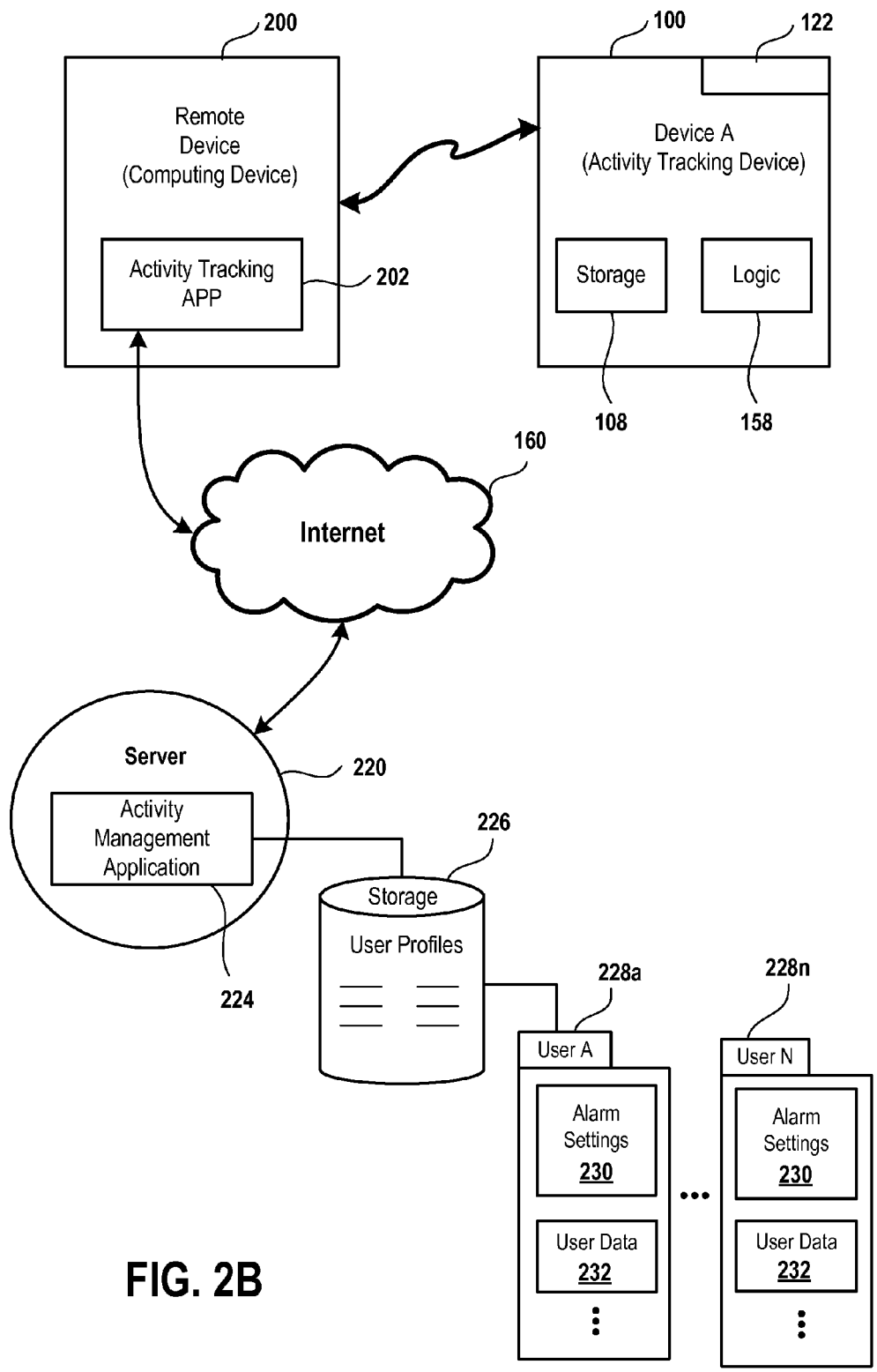
FIG. 2B illustrates an example of activity tracking device in communication with a remote device, in accordance with one embodiment of the present invention.

FIG. 2B illustrates an example of activity tracking device 100 in communication with a remote device 200. Remote device 200 is a computing device that is capable of communicating wirelessly with activity tracking device 100 and with the Internet 160. Remote device 200 can support installation and execution of applications. Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A and the Internet.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

A server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information in a user account can include, without limitation, data associated with alarm settings 230, user data, etc. As will be described in more detail below, the alarm settings 230 include information regarding a user's preferences, settings, and configurations which are settable by the user or set by default at the server 220 when accessing a respective user account. The storage 226 will include any number of user profiles, depending on the number of registered users having user accounts for their respective activity tracking devices. It should also be noted that a single user account can have various or multiple devices associated therewith, and the multiple devices can be individually customized, managed, and accessed by a user. In one embodiment, the server 220 provides access to a user to view the user data 232 associated with an activity tracking device.

Figure 3:
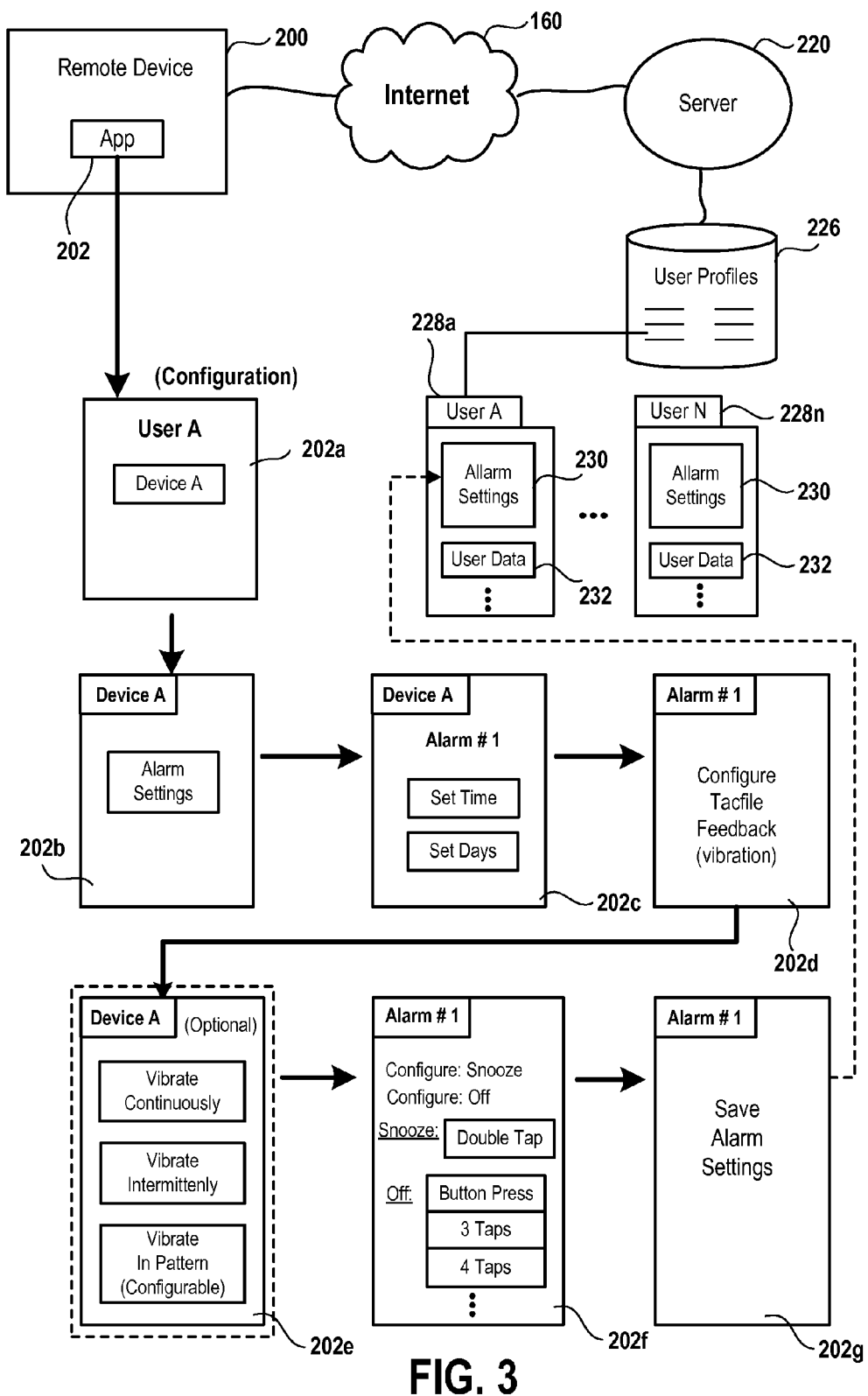
FIG. 3 is a block diagram that illustrates the configuring of alarm settings for an activity tracking device, in accordance with one embodiment of the present invention.

FIG. 3 is a block diagram that illustrates the configuring of alarm settings for an activity tracking device 100, in accordance with one embodiment of the present invention. As described above, remote device 200, e.g., a smartphone or a tablet computing device, is provided with activity tracking application 202. Both remote device 200 and also server 220 can communicate with Internet 160. Server 220 can include storage 226 that includes various user profiles associated with various user accounts. The information in the user accounts can include, among other data, data associated with alarm settings 230.

To enable a user to configure the alarm settings for an activity tracking device 100 using remote device 200, activity tracking application 202 provides a number of interfaces that allow the user to configure the alarm settings. In one embodiment, the activity tracking application 202 displays a view 202a that shows the activity tracking devices associated with the user's account. As shown in view 202a, only "Device A" is associated with User A's account. It should be appreciated, however, that additional activity tracking devices, e.g., Device B, Device C, etc., also could be associated with a user's account. A suitable GUI control, e.g., a graphic icon that can be activated by a finger touch or other user input, is used to identify each device associated with the user's account, e.g., Device A, Device B, etc., so that the user can select the device for which the alarm settings are to be configured. In the example shown in view 202a, the user would touch the "Device A" GUI control to select that device for configuration.

Once the particular device to be configured has been selected, the activity tracking application 202 displays a view 202b that shows the settings available to be selected for configuration. As shown in view 202b, only "Alarm Settings" are available to be selected for configuration. It should be appreciated, however, that other settings also could be displayed. In the example shown in view 202b, the user would touch the "Alarm Settings" GUI control to select those settings for configuration. As shown in view 202c, the activity tracking application 202 then provides GUI controls that allow the user to proceed to set an alarm time ("Set Time") and to select the days on which the alarm is to be active ("Set Days"). In the event the user touches the "Set Time" GUI control, the activity tracking application 202 displays a further view (not shown) that allows the user to set an alarm time, e.g., 6:30 am, 7:30 am, etc. In the event the user touches the "Set Days" GUI control, the activity tracking application 202 displays a further view (not shown) that allows the user to set the days on which the alarm is to be active, e.g., Monday, Tuesday, Monday thru Friday (weekdays), etc. It should be appreciated that more than one alarm, e.g., Alarm #1, Alarm #2, Alarm #3, etc., can be configured in this manner.

Once the time and days for an alarm have been set, the activity tracking application 202 provides GUI controls that allow a user to select either an audible alarm or a non-audible alarm. The non-audible alarm can be produced by tactile feedback, e.g., vibration, generated by a motor for causing vibration of the housing of the activity tracking device. The vibration can be a default vibration set by the system or, optionally, a vibration that is configured by the user. In the example shown in view 202d, the activity tracking application 202 displays a GUI control that allows the user to configure the tactile feedback (e.g., vibration) used to produce a non-audible alarm. The activity tracking application 202 then displays GUI controls that allow the user to select the nature of the vibration. In the example shown in view 202e, the GUI controls include "Vibrate Continuously," "Vibrate Intermittently," and "Vibrate in Pattern." In one embodiment, the vibration pattern is configurable, as will be described in more detail below.

As shown in view 202*f*, the activity tracking application 202 also displays GUI controls that allow a user to configure the contact gestures that can be applied to the activity tracking device to either turn the alarm off or transition the alarm into a snooze mode. In the example shown in view 202*f*, the alarm will be placed into a snooze mode when the activity tracking device detects that a surface of the activity tracking device has received a double tap (two (2) taps). Further, the alarm will be turned off when the activity tracking device detects one of the following: a button press; three (3) taps to a surface of the activity tracking device; or four (4) taps to a surface of the activity tracking device. It will be appreciated that the configuration shown in view 202*f* is an example and that this configuration can be varied to suit the needs of the user. Once the alarm settings have been configured, as shown in view 202*g*, the alarm settings are saved and the saved alarm settings 230 can be accessed by the server 220, as described above.

Figure 4:
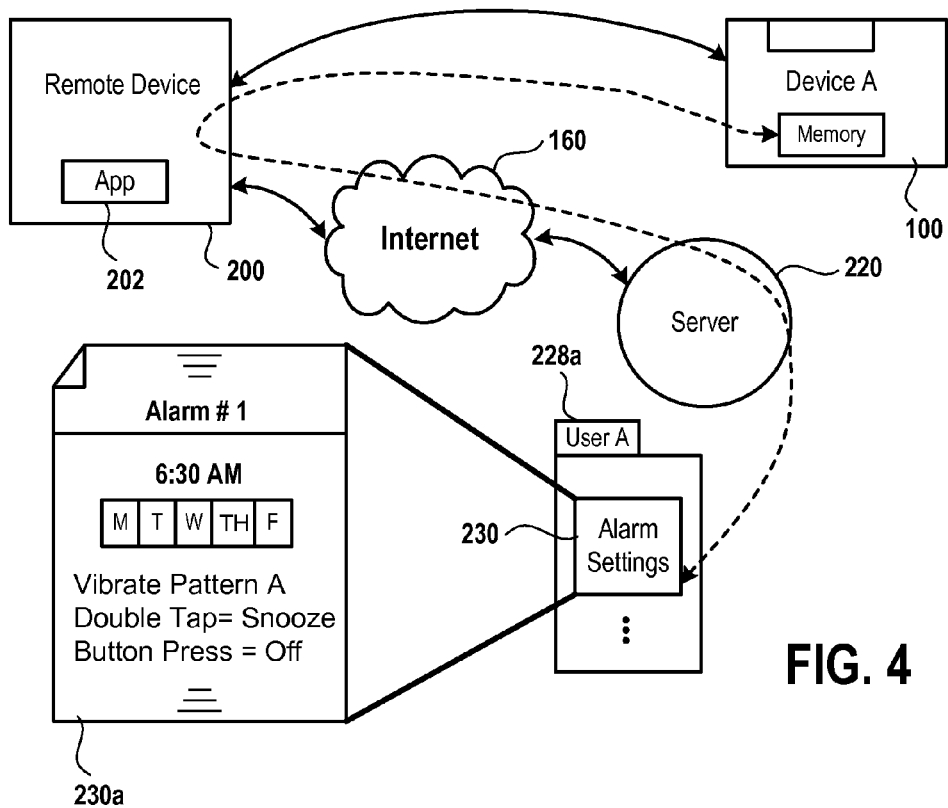
FIG. 4 is a block diagram that illustrates how the alarm settings configured using a remote device, e.g., a smartphone or tablet computing device, are made available to one or more activity tracking devices, in accordance with one embodiment of the present invention.

FIG. 4 is a block diagram that illustrates how the alarm settings configured using a remote device, e.g., a smartphone or tablet computing device, are made available to one or more activity tracking devices, in accordance with one embodiment of the present invention. As shown in FIG. 4, the configured alarm settings 230 for user account 228*a* for a User A are stored on the server 220. In the example alarm settings 230*a* shown in the figure, the alarm settings for "Alarm #1" have been set to trigger an alarm at 6:30 am on weekdays (Monday thru Friday). Further, the alarm settings have been configured to 1) trigger a non-audible alarm that uses "Vibrate Pattern A," 2) place the alarm in a snooze mode when a surface of the activity tracking device is detected to receive a "Double Tap," and 3) turn the alarm off when a button of the activity tracking device is pressed. These alarm settings can be configured using activity tracking application 202 of remote device 200, as described above with reference to FIG. 3.

The alarm settings configured using activity tracking application 202 of remote device 200 are saved to a memory of the remote device. When an Internet connection is available to remote device 200, the alarm settings are uploaded to server 220 via the Internet 160. As described above, the server 220 stores user profiles in storage 226. The alarm settings for a particular user are stored in that user's account (see, e.g., alarm settings 230 in user account 228*a* for User A). These alarm settings can be transferred to an activity tracking device 100 in several ways, as described below.

Each time the alarm settings are configured using the activity tracking application 202 of a remote device 200, the alarm settings are stored to the server 220. It is possible for a user to configure the alarm settings using multiple remote devices 200. As such, it is also possible that the alarm settings stored on a given remote device 200 might not have the most recent configuration because, e.g., the user changed the configuration of the alarm settings using a different remote device. To make sure that each remote device 200 of a user has the current alarm settings, the activity tracking application 202 on each remote device periodically synchronizes the configuration of alarm settings stored in the memory of the remote device with the configuration of the alarm settings stored on the server 220.

The alarm settings stored in the memory of a remote device 200 can be transferred to an activity tracking device 100 over a Bluetooth connection, as described above. In one embodiment, the Bluetooth connection is a low energy Bluetooth connection (e.g., Bluetooth LE, BLE, or Bluetooth Smart). Whenever an activity tracking device 100, e.g., Device A shown in FIG. 4, comes within a predefined proximity distance of a remote device 200 having an activity tracking application 202, the current alarm settings stored in the memory of the remote device are communicated to the memory of the activity tracking device over the Bluetooth connection. As a result of the synchronization process described above, the current alarm settings stored in the memory of a remote device are typically the same as the alarm settings stored on the server 220. It is possible, however, that a user could change the configuration of the alarm settings on a remote device 200 without uploading the new alarm settings to the server 220. For example, the remote device 200 might not have access to a functioning Internet connection. In this scenario, it is still possible to transfer the newly configured alarm settings from the remote device 200 to an activity tracking device 100 over the Bluetooth connection because the activity tracking application 202 stores the newly configured alarm settings to a memory of the remote device.

Figure 5:
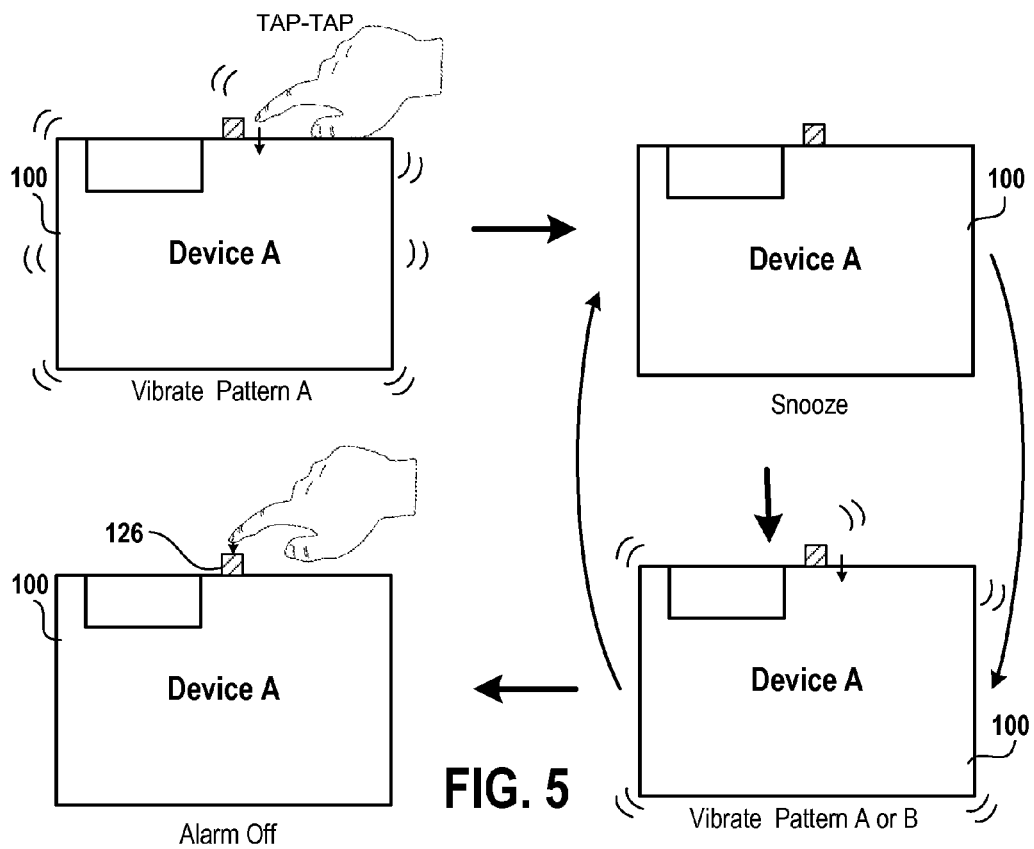
FIG. 5 is a block diagram that illustrates how the alarm of an activity tracking device can be transitioned into a snooze mode or turned off, in accordance with one embodiment of the present invention.

FIG. 5 is a block diagram that illustrates how the alarm of an activity tracking device can be transitioned into a snooze mode or turned off, in accordance with one embodiment of the present invention. In the example shown in FIG. 5, the alarm of activity tracking device 100 produces a vibration in the form of a vibration pattern referred to as "Vibrate Pattern A." When activity tracking device 100 detects that a surface of the device has received a double tap, the alarm is transitioned into a snooze mode and vibration is suspended. After a predefined snooze period, e.g., 2 minutes, 5 minutes, etc., elapses, the alarm is triggered again. In one embodiment, the alarm again produces a vibration in the form of "Vibrate Pattern A." In another embodiment, the alarm produces a vibration in the form of a different vibration pattern referred to as "Vibrate Pattern B." In the event the activity tracking device 100 detects that a surface of the device has received a double tap, the alarm will again be placed in a snooze mode. Once again, the alarm will be triggered after the predefined snooze period elapses, and the process of transitioning the alarm into a snooze mode can be repeated until the alarm is turned off. As shown in FIG. 5, the alarm can be turned off by pressing button 126 of activity tracking device 100.

Figure 6:
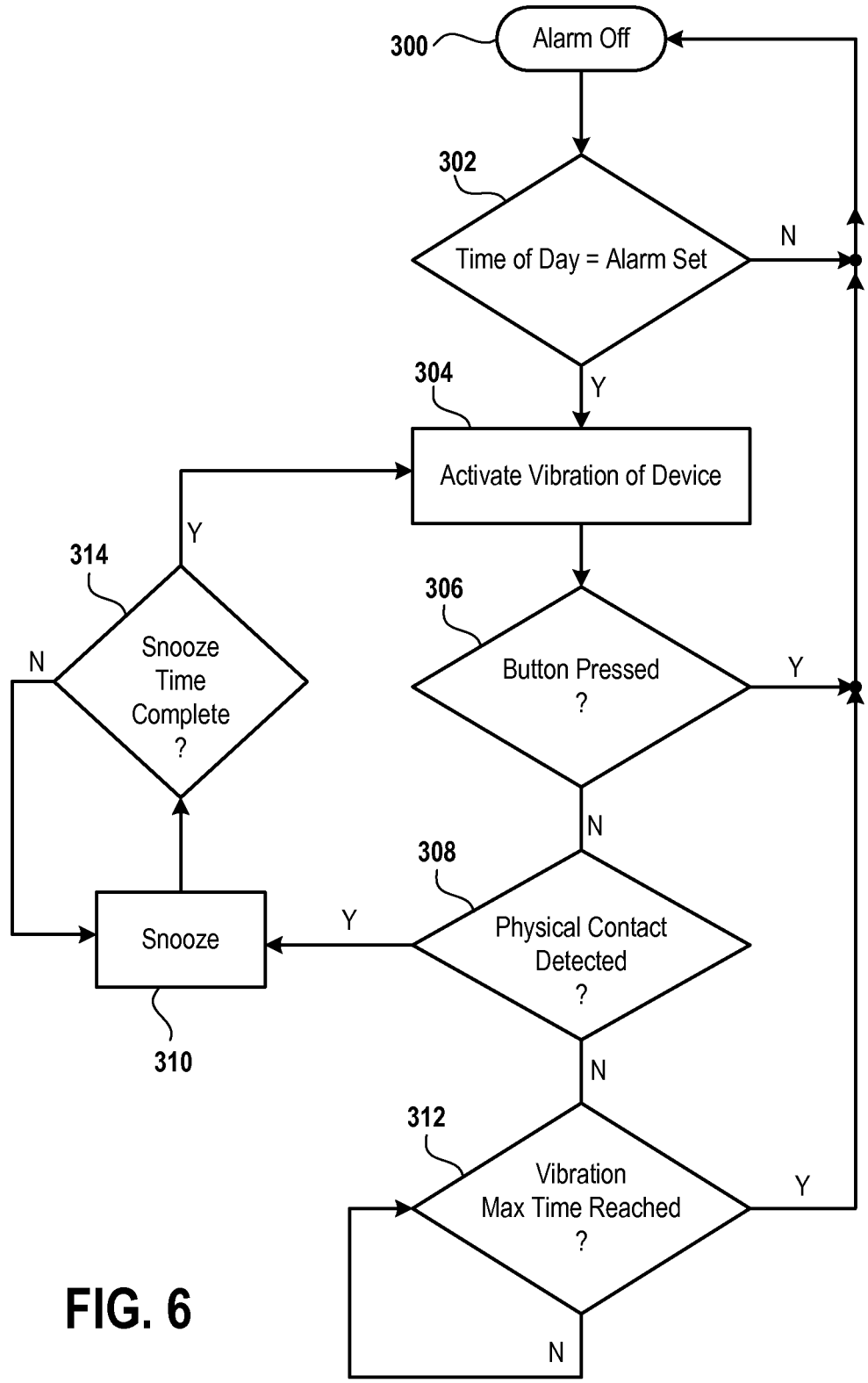
FIG. 6 is a flowchart diagram that shows the method operations performed in implementing an alarm in an activity tracking device, in accordance with one embodiment of the present invention.

FIG. 6 is a flowchart diagram that shows the method operations performed in implementing an alarm in an activity tracking device, in accordance with one embodiment of the present invention. The method begins in operation 300 in which the alarm is maintained in the "off" state. In operation 302, a determination is made as to whether the current time of day is the same as the time at which an alarm is set. If it is determined that an alarm is not set for the current time of day, then the method returns to operation 300 and the alarm continues to be maintained in the "off" mode. If it is determined that an alarm is set for the current time of day, then the method proceeds to operation 304 in which the alarm is triggered. In one embodiment, the alarm is triggered by activating vibration of the activity tracking device. As described above, the vibration may be implemented by a motor that causes vibration of the housing of the activity tracking device.

Once the alarm has been triggered, a determination is made in operation 306 as to whether a button of the activity tracking device has been pressed. If it is determined that a button of the activity tracking device has been pressed, then the alarm is turned off and the method returns to operation 300 in which the alarm is maintained in the "off" state. If it is determined that a button of the activity tracking device has not been pressed, then the method proceeds to operation 308. In operation 308, a determination is made as to whether the activity tracking device has detected physical contact with a surface thereof. In one embodiment, it is determined whether the activity tracking device has detected that a surface thereof has received a contact gesture in the form of a double tap (two (2) taps). It should be appreciated, however, that other predefined numbers of contact gestures can be detected, e.g., three (3) taps or four (4) taps. If it is determined that the activity tracking device has detected a double tap on a surface thereof, then the method proceeds to operation 310. On the other hand, if it is determined that the activity device has not detected any physical contact with a surface thereof, then the method proceeds to operation 312.

In operation 310, in response to the detected double tap on a surface of the activity tracking device, the alarm is transitioned into a snooze mode and vibration is suspended. The method then proceeds to operation 314 in which a determination is made as to whether the snooze period has elapsed. In one embodiment, the snooze period is preset by the system and lasts for a predefined period of time, e.g., 2 minutes, 3 minutes, 5 minutes, etc. In another embodiment, the snooze period is set by a user and lasts for the period of time selected by the user, e.g., 5 minutes, 10 minutes, 15 minutes, etc. If it is determined in operation 314 that the snooze period has not yet elapsed, then the method returns to operation 310 and the alarm remains in snooze mode. On the other hand, if it is determined that the snooze period has elapsed, then the method returns to operation 304 and the alarm is triggered again.

As noted above, when it is determined in operation 308 that the activity device has not detected any physical contact with a surface thereof, the method proceeds to operation 312. In operation 312, a determination is made as to whether the threshold vibration time, which is the maximum allowable vibration time, has been reached. In one embodiment, the maximum allowable vibration time is set by the system and lasts for a predefined period of time, e.g., 5 minutes, 10 minutes, 15 minutes, etc. The alarm will continue to vibrate until it is determined that the maximum allowable vibration time has been reached. Once it is determined that the maximum allowable vibration time has been reached, the alarm is turned off and the method returns to operation 300 in which the alarm is maintained in the "off" mode.

Figure 7:
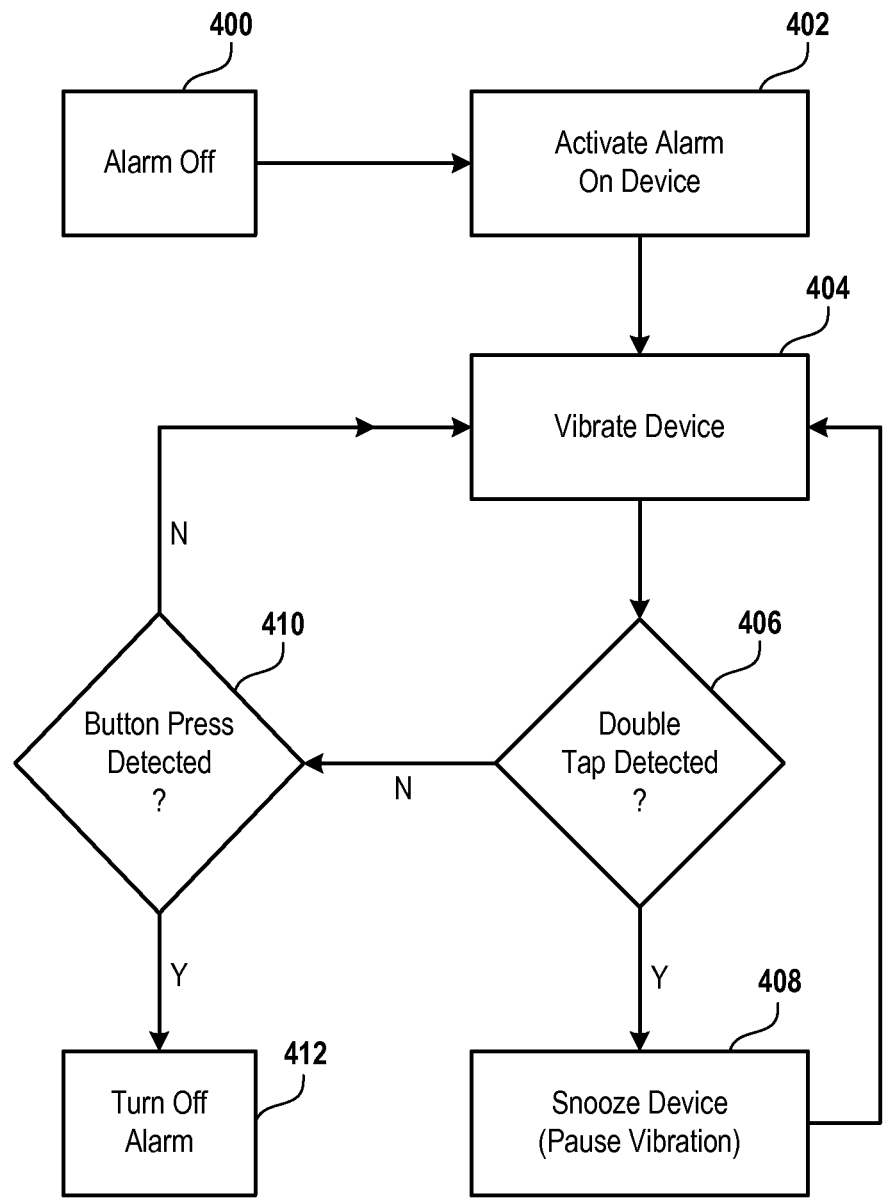
FIG. 7 is a flowchart diagram that shows the method operations performed in implementing an alarm in an activity tracking device, in accordance with another embodiment of the present invention.

FIG. 7 is a flowchart diagram that shows the method operations performed in implementing an alarm in an activity tracking device, in accordance with another embodiment of the present invention. The method begins in operation 400 in which the alarm is maintained in the "off" state. In operation 402, an alarm is activated on an activity tracking device. In response to the alarm being activated, in operation 404, the activity tracking device is vibrated. In one embodiment, the activity tracking device is continuously vibrated. In another embodiment, the activity tracking device is intermittently vibrated. In still another embodiment, the activity tracking device is vibrated in accordance with one or more vibration patterns. Once the alarm is activated, the method proceeds to operation 406 in which a determination is made as to whether the activity tracking device has detected a double tap on a surface thereof. If it is determined that a double tap has been detected, then the method proceeds to operation 408. On the other hand, if it is determined that a double tap has not been detected, then the operation proceeds to operation 410.

In operation 408, in response to the detected double tap, the alarm of the activity tracking device is transitioned into a snooze mode. In this snooze mode, the vibration of the activity tracking device is paused or suspended. When a predefined snooze period elapses, the method returns to operation 404 in which the activity tracking device is vibrated.

As noted above, when no double tap is detected in operation 406, the method proceeds to operation 410. In operation 410, a determination is made as to whether the activity tracking device has detected that a button of the device has been pressed. If it is determined that a button press has been detected, then the method proceeds to operation 412 in which the alarm is turned off. On the other hand, if no button press is detected, then the activity tracking device continues to vibrate and the method returns to operation 404 for further processing.

In the method illustrated in FIG. 7, the alarm is transitioned into a snooze mode when a double tap is detected, and the alarm is turned off when a button press is detected. It should be appreciated that the functionality of the double tap and the button press can be varied from that shown in FIG. 7. For example, the alarm could be placed in a snooze mode when a button press is detected, and the alarm could be turned off when a double tap is detected.

It should be further appreciated that, in some instances, it might not be convenient to press a button of the activity tracking device to turn an alarm off (or to place the alarm in a snooze mode). For example, a user could be engaged in an activity, e.g., running, climbing stairs, etc., and might not want to stop the activity to turn off the alarm. To address such instances, the alarm can be configured to turn off automatically based on activity detected by the activity tracking device. In one embodiment, when the alarm goes off, the activity tracking device monitors the user's current activity level. When the activity tracking device detects that the user has taken a predefined number of steps, e.g., 40 steps, 50 steps, 60 steps, etc., since the alarm went off, the alarm is turned off automatically without requiring any physical contact with the device on the part of the user. In another embodiment, when the alarm goes off, the activity tracking device not only monitor's the user's current activity level but also takes into account the user's activity level during a predefined period of time before the alarm went off, e.g., 1 minute, 2 minutes, etc. For example, if a runner had taken 90 steps in the minute before the alarm went off and the alarm was configured to turn after the user had taken 100 steps, then the alarm would be automatically turned off after the activity tracking device detected that the user had taken an additional 10 steps (for a total of 100 steps) since the alarm went off.

Figure 8:
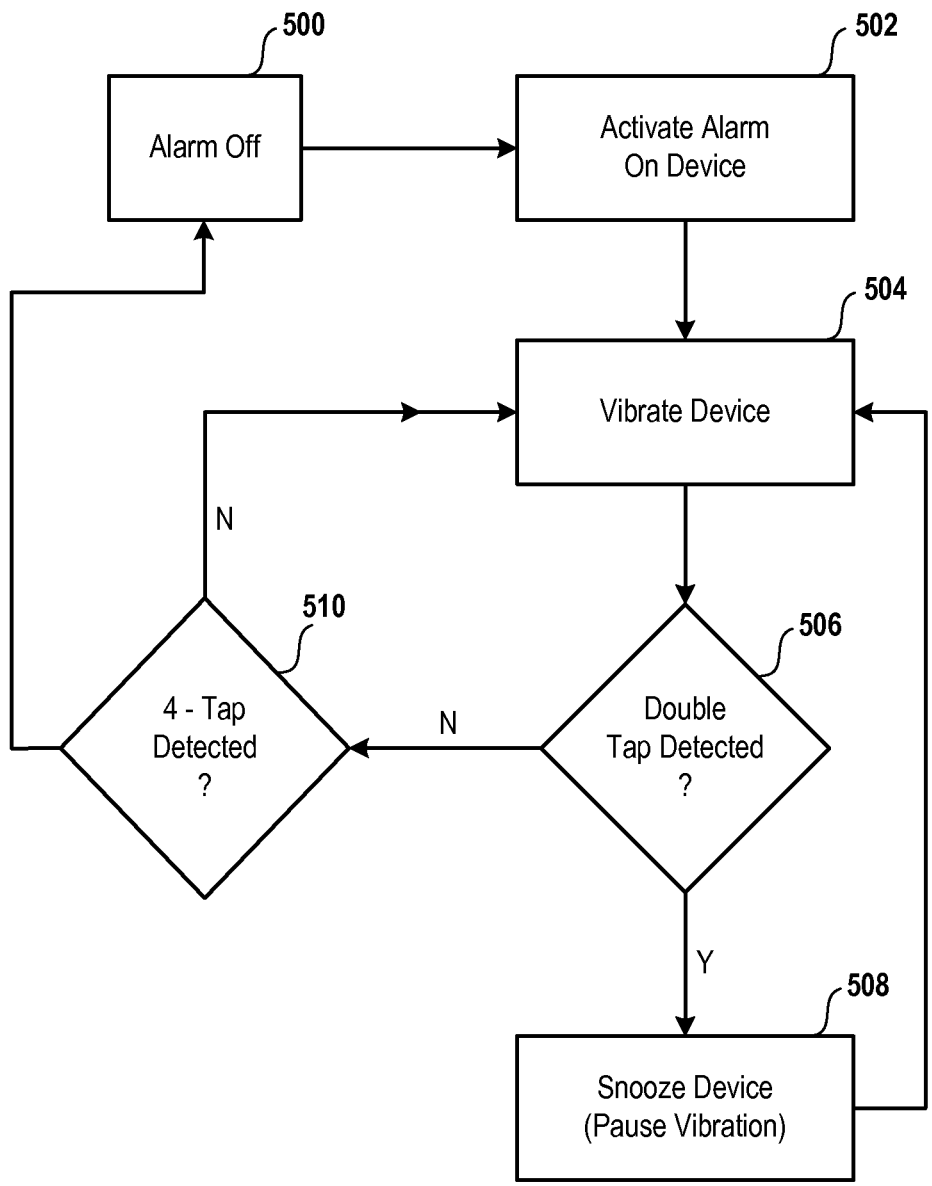
FIG. 8 is a flowchart diagram that shows the method operations performed in implementing an alarm in an activity tracking device, in accordance with yet another embodiment of the present invention.

FIG. 8 is a flowchart diagram that shows the method operations performed in implementing an alarm in an activity tracking device, in accordance with yet another embodiment of the present invention. The method shown in FIG. 8 does not require the use of a button press to turn the alarm off. Consequently, this method can be implemented in activity tracking devices that do not include a button. The method begins in operation 500 in which the alarm is maintained in the "off" state or the "off" mode. In operation 502, an alarm is activated on an activity tracking device. In response to the alarm being activated, in operation 504, the activity tracking device is vibrated. Once the alarm is activated, the method proceeds to operation 506 in which a determination is made as to whether the activity tracking device has detected a double tap on a surface thereof. If it is determined that a double tap has been detected, then the method proceeds to operation 508. On the other hand, if it is determined that a double tap has not been detected, then the operation proceeds to operation 510.

In operation 508, in response to the detected double tap, the alarm of the activity tracking device is transitioned into a snooze mode. In this snooze mode, the vibration of the activity tracking device is paused or suspended. When a predefined snooze period elapses, the method returns to operation 504 in which the activity tracking device is vibrated.

As noted above, when no double tap is detected in operation 506, the method proceeds to operation 510. In operation 510, a determination is made as to whether the activity tracking device has detected four (4) taps ("a four tap") on a surface of the activity tracking device. If it is determined that a four tap has been detected, then the alarm is turned off and the method returns to operation 500 in which the alarm is maintained in the "off" state. On the other hand, if no four tap is detected, then the activity tracking device continues to vibrate and the method returns to operation 504 for further processing.

Figure 9:
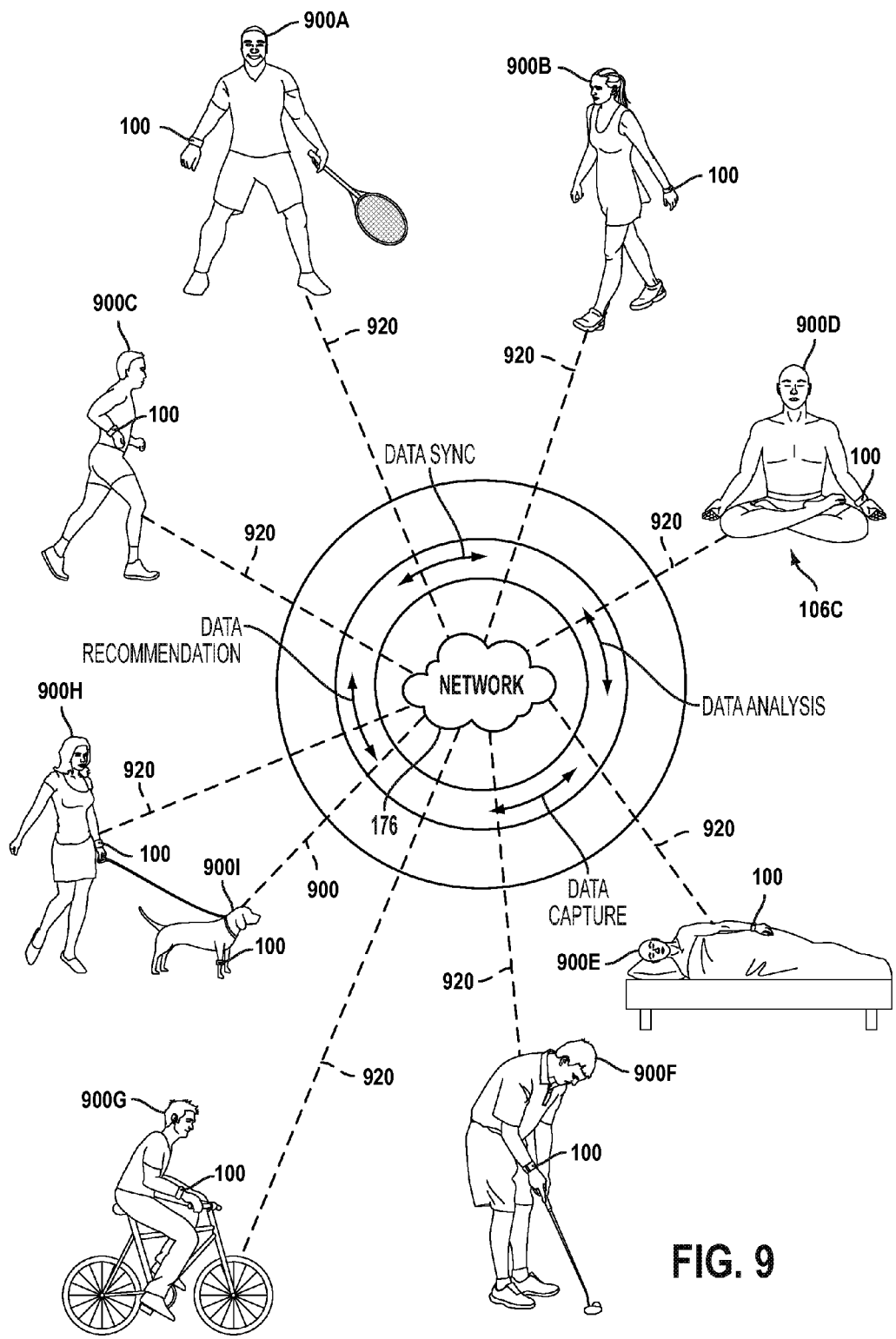
FIG. 9 illustrates an example where various types of activities of users can be captured by activity tracking devices, in accordance with one embodiment of the present invention.

FIG. 9 illustrates an example where various types of activities of users 900A-900I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 920 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smartphone or tablet or smartwatch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated with the user's account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smartphone.

In one embodiment, the data captured by the activity tracking device 100 is received by the computing device, and the data is synchronized with the activity measured application on the server. In this example, data viewable on the computing device (e.g. smartphone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the user's device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method, comprising:
receiving an alarm setting that defines a time of day for triggering an alarm on a device for tracking activity data of a user;
activating the alarm upon reaching the time of day defined by the alarm setting, the alarm producing a vibration of the device;
using a sensor to detect a physical contact upon the device; and
deactivating the alarm if the physical contact qualifies as an input to deactivate the alarm, the deactivating causing the vibration of the device to be suspended, wherein the method is executed by a processor.

2. The method of claim 1, wherein the vibration being suspended transitions the alarm into one of a snooze mode or an off mode.

3. The method of claim 2, wherein the snooze mode continues for a predetermined period of time before reactivating the alarm; and the method further includes:
transitioning into the snooze mode one or more times until entering the off mode or processing the vibration for a threshold period of time.

4. The method of claim 1, wherein the physical contact is a result of one or more contact gestures on a surface of the device, wherein the contact gestures are in a form of one or more slides on the surface of the device, or one or more rubs on the surface of the device.

5. The method of claim 4, wherein a snooze mode is entered which causes the vibration to be suspended when the physical contact is represented by one of,
a single contact gesture on a surface of the device; or
a double contact gesture on the surface of the device; or
three contact gestures on the surface of the device; or
four contact gestures on the surface of the device; or
a predetermined set of repeated contact gestures on the surface of the device.

6. The method of claim 5, wherein two or more of the contact gestures are received within a predetermined period of time to qualify as the input.

7. The method of claim 5, further comprising:
transitioning from the snooze mode to an off mode when an additional physical contact is sensed by the sensor, wherein the physical contact is represented by one of,
a single contact gesture on a surface of the device; or
a double contact gesture on the surface of the device; or
three contact gestures on the surface of the device; or
four contact gestures on the surface of the device; or
a predetermined set of repeated contact gestures on the surface of the device.

8. The method of claim 7, wherein two or more of the contact gestures are received within a predetermined period of time to qualify as the input.

9. The method of claim 5, further comprising:
transitioning from the snooze mode to an off mode when the processor of the device determines that a button of the device is pressed.

10. The method of claim 1, wherein the alarm setting is received wirelessly from a computing device.

11. The method of claim 10, wherein the alarm setting is transferred from a server to the computing device over the Internet and from the computing device to the device via a wireless Bluetooth connection.

12. A device configured for capture of activity data for a user, comprising:
a housing;
a sensor disposed in the housing to capture physical contact upon the housing;
a motor for causing vibration of the housing of the device;
a memory for storing an alarm setting that defines a time of day for triggering an alarm on the device; and
a processor for activating the alarm upon reaching the time of day defined by the alarm setting, the alarm causing the motor to produce the vibration of the housing, the sensor being interfaced with the processor and configured to detect a physical contact upon the housing of the device, the processor configured to deactivate the alarm if the physical contact qualifies as an input to deactivate the alarm, the deactivating causing the vibration of the device to be suspended.

13. The device of claim 12, wherein the housing is part of a wearable wrist attachable structure, or an attachable structure that can be carried or worn by the user.

14. The device of claim 12, wherein the physical contact captured by the sensor is from one or more contact gestures upon the housing by a finger or hand.

15. The device of claim 12, wherein the housing includes a button, the physical contact upon the housing not being from a button press.

16. The device of claim 12, wherein the wearable wrist attachable structure is defined at least partially from a plastic material.

17. The device of claim 12, wherein the housing further includes wireless communication logic.

18. The device of claim 17, wherein the wireless communication logic includes one of WiFi processing logic, or Bluetooth (BT) processing logic, or radio processing logic.

19. The device of claim 17, wherein the wireless communication logic is configured to pair with a portable computing device or a computer, and the portable computing device or the computer is configured for communication over the Internet with a server, the server having processing instructions for configuring the alarm settings.

20. The device of claim 12, wherein the vibration being suspended transitions the alarm into one of a snooze mode or an off mode.

21. The device of claim 20, wherein the processor configures the snooze mode to continue for a predetermined period of time before reactivating the alarm, and the processor transitions into the snooze mode one or more times until entering the off mode or processing the vibration for a threshold period of time.

22. The device of claim 14, wherein two or more contact gestures on a surface of the device are received within a predetermined period of time to qualify as the input.

23. One or more non-transitory computer readable media including instructions which, when executed by a processor, perform the following operations:
receiving an alarm setting that defines a time of day for triggering an alarm on a device for tracking activity data of a user;
activating the alarm upon reaching the time of day defined by the alarm setting, the alarm producing a vibration of the device;
using a sensor to detect a physical contact upon the device; and
deactivating the alarm if the physical contact qualifies as an input to deactivate the alarm, the deactivating causing the vibration of the device to be suspended.

24. The computer readable media of claim 23, wherein the vibration being suspended transitions the alarm into one of a snooze mode or an off mode.

25. The computer readable media of claim 24, wherein the snooze mode continues for a predetermined period of time before reactivating the alarm; and the operations performed further include:
transitioning into the snooze mode one or more times until entering the off mode or processing the vibration for a threshold period of time.

26. The computer readable media of claim 23, wherein the physical contact is a result of one or more contact gestures on a surface of the device, wherein the contact gestures are in a form of one or more slides on the surface of the device, or one or more rubs on the surface of the device.

27. The computer readable media of claim 26, wherein a snooze mode is entered which causes the vibration to be suspended when the physical contact is represented by one of,
- a single contact gesture on a surface of the device; or
- a double contact gesture on the surface of the device; or
- three contact gestures on the surface of the device; or
- four contact gestures on the surface of the device; or
- a predetermined set of repeated contact gestures on the surface of the device.

28. The computer readable media of claim 27, wherein two or more of the contact gestures are received within a predetermined period of time to qualify as the input.

29. The computer readable media of claim 27, wherein the operations performed further include:
- transitioning from the snooze mode to an off mode when an additional physical contact is sensed by the sensor, wherein the physical contact is represented by one of,
- a single contact gesture on a surface of the device; or
- a double contact gesture on the surface of the device; or
- three contact gestures on the surface of the device; or
- four contact gestures on the surface of the device; or
- a predetermined set of repeated contact gestures on the surface of the device.

30. The computer readable media of claim 29, wherein two or more of the contact gestures are received within a predetermined period of time to qualify as the input.

* * * * *